United States Patent
Wang et al.

(10) Patent No.: US 10,994,051 B2
(45) Date of Patent: May 4, 2021

(54) KERATOPROSTHESIS IMPLANTING METHOD

(71) Applicants: Liqiang Wang, Beijing (CN); Yifei Huang, Beijing (CN)

(72) Inventors: Liqiang Wang, Beijing (CN); Yifei Huang, Beijing (CN)

(*) Notice: Subject to any disclaimer, the term of this patent is extended or adjusted under 35 U.S.C. 154(b) by 105 days.

(21) Appl. No.: 16/553,500

(22) Filed: Aug. 28, 2019

(65) Prior Publication Data
US 2021/0060207 A1   Mar. 4, 2021

(51) Int. Cl.
*A61F 2/14* (2006.01)
*A61L 27/36* (2006.01)
*A61F 9/007* (2006.01)

(52) U.S. Cl.
CPC .......... *A61L 27/3612* (2013.01); *A61F 2/142* (2013.01); *A61F 2/148* (2013.01); *A61F 2/15* (2015.04); *A61F 9/00781* (2013.01); *A61L 2430/16* (2013.01); *A61L 2430/40* (2013.01)

(58) Field of Classification Search
CPC ... A61F 2/142; A61F 9/00781; A61L 2430/16
See application file for complete search history.

(56) References Cited

U.S. PATENT DOCUMENTS 9,974,646 B2 * 5/2018 Parel ................ A61F 2/142

OTHER PUBLICATIONS

Yuan, Ji et al. "The effects of transplantation of compound keratoprosthesis in clinical practice and management of complications after operation". Chinese Journal of Ophthalmology 45.2:104-109. Chinese Medical Association. (Feb. 2009).*

* cited by examiner

*Primary Examiner* — Jerrah Edwards
*Assistant Examiner* — Javier G Blanco
(74) *Attorney, Agent, or Firm* — Larson & Larson, P.A.; Justin P. Miller; Frank Liebenow

(57) ABSTRACT

A modified, novel surgical technique of Boston Keratoprosthesis (B-KPro) Type II is provided to restore the visual acuity in patients with bilateral end-stage ocular surface disorders, comprising 1) Preparing auricular cartilage; 2) Exposing corneal stroma and sclera surface and removing the corneal epithelium; 3) Assembling the keratoprosthesis device; 4) Implanting the assembled device into recipient cornea; 5) Implanting the autologous cartilage; and 6) Suturing the Tenon's capsule and conjunctiva to the ocular surface layer by layer to cover and reinforce the KPro.

5 Claims, 2 Drawing Sheets

KERATOPROSTHESIS IMPLANTING METHOD

FIELD

This invention relates to the field of eye surgery and more particularly to a method for implantation of a keratoprosthesis.

BACKGROUND

The present invention relates to a modified surgical technique of B-KPro Type II with autologous auricular cartilage reinforcement to decrease the postoperative complications.

Extensively keratinized ocular surface caused by severe dry eye diseases contributed to an irreversible corneal opacification and vascularization, in which keratoprosthesis (KPro) is the only salvage procedure to restore the patients' vision. B-KPro Type II provides a potential solution for such patients to restore vision. However, sediment or debris often develops around the KPro stem, and it causes further KPro extrusion, development of retroprosthesis membrane, endophthalmitis, and other postoperative complications. Therefore, modification to KPro procedure is focused on trying every possible to persevere the vision and to improve the bio-integration of KPro, which could further reduce the complications.

SUMMARY

Accordingly, it is an object of the present invention to provide a method of implanting keratoprosthesis, especially an improved method to modify based on B-KPro Type II.

A modified, novel surgical technique of Boston Keratoprosthesis (B-KPro) Type II is provided to restore the visual acuity in patients with bilateral end-stage ocular surface disorders, comprising 1) Preparing auricular cartilage; 2) Exposing corneal stroma and sclera surface and removing the corneal epithelium; 3) Assembling the keratoprosthesis device; 4) Implanting the assembled device into recipient cornea; 5) Implanting the autologous cartilage; and 6) Suturing the Tenon's capsule and conjunctiva to the ocular surface layer by layer to cover and reinforce the KPro.

In this modification, the autologous auricular cartilage is firstly prepared to fit the optic stem and then placed and wrapped around the protruding stem to replace the role of the eyelid flap in B-KPro Type II. In addition, to further enforce the device, conjunctiva, mucosa, or skin flap is used to cover the auricular cartilage to the nub. The key part of this novel improvement is that the covering tissue around the B-KPro stem is replace to cartilage rather than the eyelid, and this shrinks the gap between the tissue and the stem, decreases the probability of epithelium down grow, device extrusion, retroprosthesis membrane development and thus reduces the incidence of postoperative complications such as endophthalmitis.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION

Figure 1:
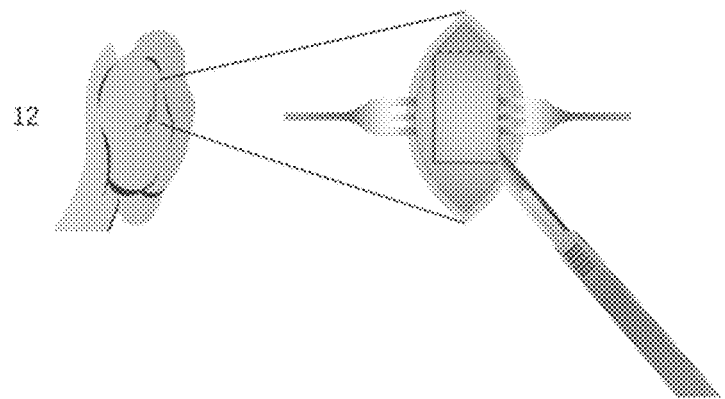
FIG. 1 is a schematic diagram of the auricular cartilage preparation.

Briefly, the method of present invention comprises six steps:
1. Auricular cartilage preparation;
2. Corneal stroma and sclera surface exposure;
3. Standard assembly of B-KPro Type II device;
4. Implantation of the assembled device into recipient cornea;
5. Reinforcement with the autologous cartilage; and
6. Tenon's capsule and conjunctiva were sutured to the ocular surface layer by layer to cover and reinforce the KPro.

The following reference numbers are used throughout the drawings:
1. Optical cylinder
2. Bulbar conjunctiva or oral mucosa
3. Tennon's capsule
4. Host cornea
5. Autologous auricular cartilage
6. Donor cornea
7. Back plate
8. Allogenic corneoscleral ring
9. 10-0 Nylon suture
10. 7-0 Prolene
11. Sclera
12. Auricle Before operation, all patients shall receive general anesthesia.

Referring to FIG. 1:

Step 1. Auricular cartilage preparation (FIG. 1). A 15 mm vertical skin incision is made on the superior one-fourth of the dorsal side of the ipsilateral ear and subcutaneous tissue is dissected to expose the cartilage. A 12×10 mm cartilage is harvested for later use.

Step 2. Corneal stroma and sclera surface exposure. The conjunctival tissue is separated, and the cornea and sclera tissue are fully exposed 5 mm from the limbus, which is conveniently prepared for subsequent corneal surgery and vitrectomy. For patients with no conjunctival sac, the technique is similar to the conventional B-KPro Type II (i.e. through the eyelid skin). For patients with limited conjunctival sac, the attempt should be made to dissect and preserve the conjunctival tissue and corneal pannus (through conjunctiva).

Figure 2:
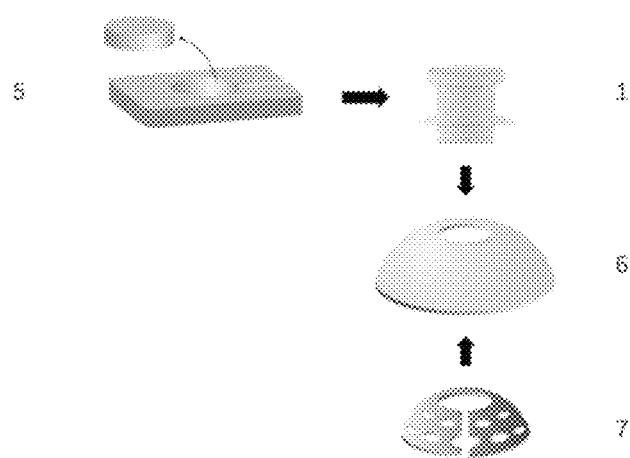
FIG. 2 is a schematic diagram of the B-KPro Type II complex assembly.

Referring to FIG. 2:

Step 3. B-KPro Type II complex installation (FIG. 2).[1, 4] In brief, donor corneal epithelium is removed. A 8.5-9.0 mm cornea carrier with 3 mm central hole is obtained by trephination (usually the cornea carrier is 0.5-1.0 mm larger than the recipient bed). If autologous cornea is used, an 8 mm button with a 2.75 mm central hole is suitable for the implantation. Optical cylinder, donor cornea and titanium back plate are assembled in the bottom-up order. It is essential to make sure that the back plate shall slide into its groove on the stem.

Step 4. B-KPro Type II device implantation. The host cornea is trephined, and the lens is extracted in the phakic eye. The KPro device is sutured in place as it does in standard penetrating keratoplasty. Anterior vitrectomy is performed by PPV (pars plana vitrectomy) with a 25G system. Meanwhile, the fundus, including macular and optic disc, is clinically assessed. Glaucoma drainage devices (GDDs) can be simultaneously implanted depending on whether the patient was diagnosed glaucoma pre-operation [5, 6].

Figure 3:
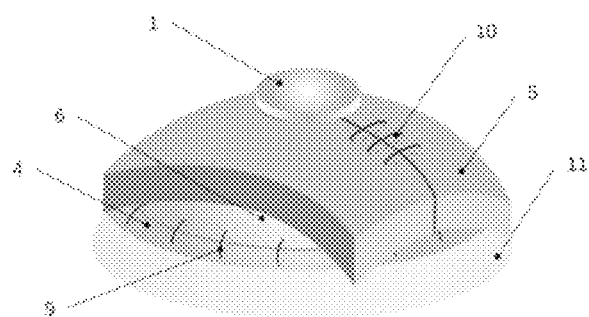
FIG. 3 is a schematic diagram of reinforcement with cartilage.

Referring to FIG. 3:

Step 5. Reinforcement with cartilage (FIG. 3). The autologous auricular cartilage is trimmed to the desired shape to fit the ocular surface, and a 3 mm central hole is trephined to sit the optic cylinder. A radial incision is made for the cartilage to wrap around the optic cylinder and then the incision is sutured, and the cartilage is further anchored to the ocular surface with 7-0 prolene sutures. To achieve a better result, the edge of the cartilage shall be covered with an allogenic corneoscleral ring, which is sutured on the host sclera.

Figure 4:
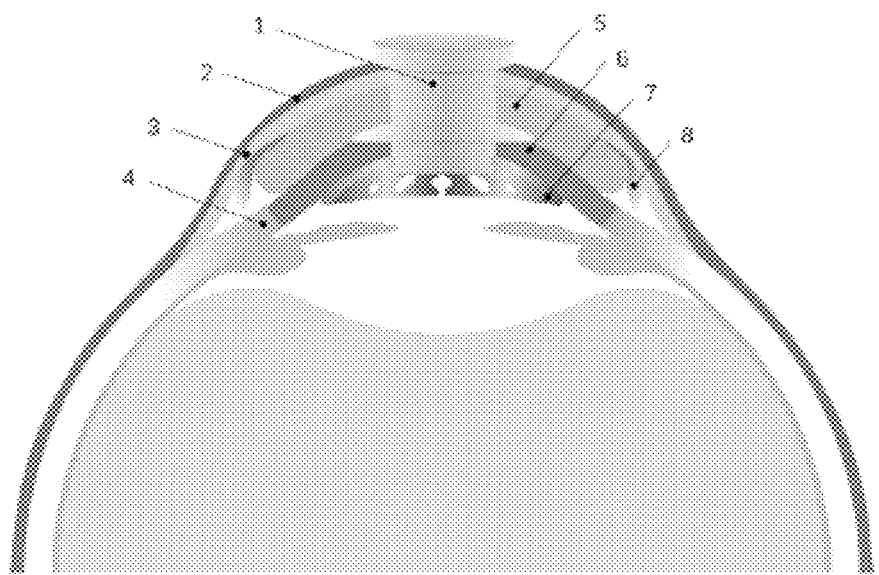
FIG. 4 is a schematic illustration of implanted B-KPro Type II with modified autologous auricular cartilage reinforcement.

Referring to FIG. 4:

Step 6. Tenon's capsule and conjunctiva are sutured to the ocular surface layer by layer to further cover and reinforce the KPro device (FIG. 4). If the conjunctival sac is inadequate, eyelid skin without tarsus can be used to cover the ocular surface and allow the Kpro nub to protrude through the closed eyelid. If the surgeon would like to cover the eye with mucosa, reconstruction conjunctival sac with buccal mucosa can be used instead, preoperatively.

Postoperative management includes wide-spectrum topical antibiotics (fourth-generation fluoroquinolone 0.3% gatifloxacin q.i.d. indefinite) and in together with topical steroids for certain period of time.

The B-Kpro Type II procedure provides a surgical option for patients with severe ocular surface diseases who would fail other types of corneal surgery. However, the incidences of postoperative complications are high, and the surgical procedure is quite complicated compared to Type I procedure.

Other alternative surgical interventions that have been proven to be effective in eyes with severe dry ocular surface diseases such as autoimmune diseases and chemical insults are the osteo-odonto-keratoprosthesis (OOKP)[7] and Tibial bone KPro[8]. Current findings suggest the OOKP and Tibial bone KPro have a better long-term prognosis compared to the Boston KPro.[9, 10] However, OOKP procedure is extraordinarily demanding and time-consuming (Two or three-stage surgeries with intervals of several months) and it also places an enormous burden on the patients and the surgical team that requires both experienced oral and maxillofacial surgeon and corneal specialists. For those disadvantages, the further popularization of OOKP and tibial KPro is limited.

Our surgical scheme on Boston KPro type II is inspired by OOKP, which used a single-rooted tooth and its surrounding intact alveolar bone to fashion a plate as a carrier for the PMMA optical cylinder[11]. We used autologous auricular cartilage in our procedures as the reinforcing part so one surgeon could easily finish the whole procedure. In addition, it takes only one stage to finish, and the operation time is significantly less than OOKP. At the same time, it also prominently alleviates the pain of patients receiving tooth extraction.

First of all, harvesting autologous auricular cartilage is easy to perform and less harmful to the patient than tooth extraction. Also, cartilage is an avascular tissue, so the survival of chondrocyte does not require a direct blood flow, thus it suits the relatively low blood supply environment in the cornea and will reduce the gap between the stem and the tissue and effectively increase the proportions of retention rates of the KPro device. The down-growing skin happens in routine BKPro type II procedure and it would further expand the original gap and causes the loosing of the optical stem, which eventually would lead to device extrusion and possibly endophthalmitis. The malleable cartilage tissue we used in this new technique can fully fit with the rigid PMMA optical stem, which would prevent the down growing of the skin along the optical stem.

Secondly, our surgical scheme uses conjunctiva or oral mucosa to further cover the ear cartilage surface, which not only provides a nutritional support for cartilage to prevent the cartilage melting caused by severe dry eyes, but also enables the transplanted tissues to stick together with the eyeball, thus resolves the "shaking effect" of traditional KPro under eye movement.

Thirdly, the secreted sebum from covering skin tissue around the eyelid often affects patient's visual perception and our procedure does not involve the skin covering and avoid this post-operative complication.

Fourthly, the surgery can be finished just in one procedure and recovery visual function at the same time instead of separating into two or three periods which happened in OOKP or MICOF Kpro, especially in refractory keratohelcosis, perforation or Kpro cornea carrier melting cases.

To date, we are the first to propose this novel modification to B-KPro Type II, which maximizes the advantages of the artificial cornea over the past few decades. It is necessary to evaluate its efficacy further and long-term prognosis. Clinical studies are underway to evaluate the prevention of aqueous leakage, incidences of postoperative complication, further management, and etc. Since most of our patients received this procedure within a year, we have not yet critically evaluated the mid-term and long-term visual outcomes and the development of related complications. However, early stage data showed it is encouraging and promising.

REFERENCES CITED ABOVE

[1] RUDNISKY C J, BELIN M W, GUO R, et at Visual Acuity Outcomes of the Boston Keratoprosthesis Type 1: Multicenter Study Results [J]. American journal of ophthalmology, 2016, 162(89-98.e1.

[2] LEE R, KHOUEIR Z, TSIKATA E, et al. Long-term Visual Outcomes and Complications of Boston Keratoprosthesis Type II Implantation [J]. Ophthalmology, 2017, 124(1): 27-35.

[3] IYER G, SRINIVASAN B, AGARWAL S, et al. Boston Type 2 keratoprosthesis-mid term outcomes from a tertiary eye care centre in India [J]. The ocular surface, 2019, 17(1): 50-4.

[4] PUJARI S, SIDDIQUE S S, DOHLMAN C H, et al. The Boston keratoprosthesis type II: the Massachusetts Eye and Ear Infirmary experience [J]. Cornea, 2011, 30(12): 1298-303.

[5] MS C, FI K, C B, et al. Staged ocular fornix reconstruction for glaucoma drainage device under neoconjunctiva at the time of Boston type 1 Keratoprosthesis implantation [J]. 2019, 17(2): 336-40.

[6] TL L, SY C, SK L, et al. Safety of Concurrent Boston Type I Keratoprosthesis and Glaucoma Drainage Device Implantation [J]. 2017, 124(1): 12-9.

[7] TAN A, TAN D T, TAN X W, et al. Osteo-odonto keratoprosthesis: systematic review of surgical outcomes and complication rates [J]. The ocular surface, 2012, 10(1): 15-25.

[8] CHAROENROOK V, MICHAEL R, DE LA PAZ M F, et al. Comparison of long-term results between osteoodonto-keratoprosthesis and tibial bone keratoprosthesis [J]. The ocular surface, 2018, 16(2): 259-64.

[9] DE LA PAZ M F, SALVADOR-CULLA B, CHAROENROOK V, et al. Osteo-odonto-, Tibial bone and Boston keratoprosthesis in clinically comparable cases of chemical injury and autoimmune disease [J]. The ocular surface, 2019,

[10] HILLE K, GRABNER G, LIU C, et al. Standards for modified osteoodontokeratoprosthesis (OOKP) surgery according to Strampelli and Falcinelli: the Rome-Vienna Protocol [J]. Cornea, 2005, 24(8): 895-908.

[11] CHAROENROOK V, MICHAEL R, DE LA PAZ M F, et al. Osteokeratoprosthesis Using Tibial Bone: Surgical Technique and Outcomes [J]. The ocular surface, 2016, 14(4): 495-506.

The features and advantages described herein are not all-inclusive and in particular, many additional features and advantages will be apparent to one of the ordinary skilled in the art in view of the drawings, specification, and claims. Moreover, it shall be noted that eh language used in the specification has been selected principally for readability and instructional purposes, and not to limit the scope of the inventive subject-matter described herein. The foregoing description for the embodiments of the disclosure has been presented for the purpose of illustration; it is not intended to be exhaustive or to limit the claims to the precise forms disclosed. Persons skilled in the relevant art can appreciate that many modifications and variations are possible in light of the above disclosure.

What is claimed is:

1. A method of implanting a keratoprosthesis device into a recipient cornea of a patient's eye, the method comprising:
    Preparing autologous auricular cartilage;
    Exposing corneal stroma and sclera surface and removing the corneal epithelium;
    Separating Tenon's capsule and Bulbar conjunctiva for subsequent suturing;
    Assembling the keratoprosthesis device;
    Implanting the assembled keratoprosthesis device into the recipient cornea;
    Implanting the autologous auricular cartilage over the implanted keratoprosthesis device; and
    Suturing the Tenon's capsule and Bulbar conjunctiva to an ocular surface, layer by layer, to cover and reinforce the implanted autologous auricular cartilage and keratoprosthesis device,
    wherein the autologous auricular cartilage is trimmed to fit the ocular surface, and a 3 mm central hole is preoperatively trephined in the autologous auricular cartilage to sit an optic cylinder of the keratoprosthesis device within said central hole,
    wherein the keratoprosthesis device is a Boston Keratoprosthesis (B-KPro) Type II device.

2. The method of claim 1, wherein the autologous auricular cartilage is harvested in the size of 12×10 mm.

3. The method of claim 1, further including implanting a glaucoma drainage device.

4. The method of claim 1, wherein a radial incision is made for the autologous auricular cartilage to wrap around the optic cylinder in the keratoprosthesis device and then the incision is sutured, and the autologous auricular cartilage is further anchored to the ocular surface with 7-0 prolene sutures.

5. The method of claim 1, wherein an edge of the autologous auricular cartilage is covered with an allogenic corneoscleral ring, which is sutured on the sclera of the patient's eye.

* * * * *